United States Patent [19]

Kuriowa et al.

[11] Patent Number: 4,983,756
[45] Date of Patent: Jan. 8, 1991

[54] NOVEL CHOLINE DERIVATIVE AND METHOD FOR DETEMINING SERUM CHOLINESTERASE ACTIVITY USING THE SAME

[75] Inventors: Katsumasa Kuroiwa; Katsuhiro Katayama, both of Koriyama; Takeshi Nagasawa, Urawa, all of Japan

[73] Assignee: Nitto Boseki Co., Ltd., Fukushimashi, Japan

[21] Appl. No.: 311,329

[22] Filed: Feb. 15, 1989

[30] Foreign Application Priority Data

Feb. 24, 1988 [JP] Japan .................................. 63-41375

[51] Int. Cl.$^5$ ............................ C07C 9/76; C12Q 1/46
[52] U.S. Cl. .......................................... 560/56; 435/20
[58] Field of Search ............................. 560/56; 435/20

[56] References Cited

U.S. PATENT DOCUMENTS

| 4,218,453 | 8/1980 | Hannart | 514/224.5 |
| 4,401,827 | 8/1983 | deWitt | 560/56 |
| 4,496,755 | 1/1985 | Tsuehihashi et al. | 560/56 |
| 4,582,855 | 4/1986 | Kam et al. | 560/56 |

FOREIGN PATENT DOCUMENTS

| 289262 | 11/1988 | European Pat. Off. . |
| 138533 | 10/1979 | Japan . |
| 110198 | 7/1982 | Japan . |
| 129999 | 8/1983 | Japan . |
| 1031749 | 2/1989 | Japan . |
| 1022033 | 3/1966 | United Kingdom . |

OTHER PUBLICATIONS

R. Ammon, Pflugers Arch. Ges Physiol., 223,487 (1933).
H. O. Michel et al., J. Lab. & Clin. Med., 34,1564 (1949).
H. Takahashi et al., Medicine and Biology, 20,96 (1951).
H. G. Biggs et al., Am. J. Clin. Pathol., 30,181 (1958).
T. Sasaki, Chemical Pathology, 12, 555 (1964).
P. Garry et al., J. Clin. Chem. 11,(2),91 (1965).
H. Okabe et al., Clinical Pathology, 25,751 (1977).
W. Kalow et al., Can. J. Biochem. Physiol., 35, 339 (1957).

Primary Examiner—Paul J. Killos
Attorney, Agent, or Firm—Darby & Darby

[57] ABSTRACT

A novel compound, 6-acetoxymethyl-2-naphthoylcholine halide, is very stable to nonenzymatic hydrolysis and react specifically with cholinesterase in serum. A UV method for determining cholinesterase activity in serum which uses the novel compound as a substrate permits very accurate and highly reproducible determination of cholinesterase activity in serum, and therefor is very useful for clinical examination.

4 Claims, 4 Drawing Sheets

F I G. 1
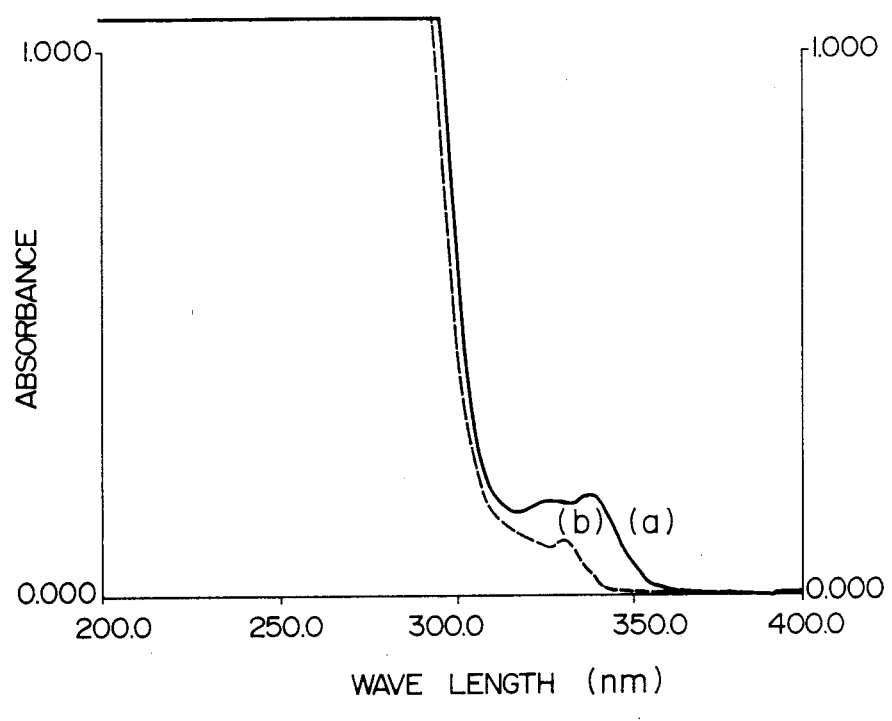

NOVEL CHOLINE DERIVATIVE AND METHOD FOR DETEMINING SERUM CHOLINESTERASE ACTIVITY USING THE SAME

FIELD OF THE INVENTION

This invention relates to a novel choline derivative represented by the general formula (I):

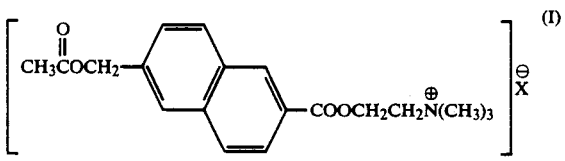

wherein X is a halogen atom, and a method for determination of cholinesterase activity in serum, characterized by using the same as a substrate.

The determination method of this invention permits easy and simple determination of cholinesterase activity, and is very useful for clinical examinations of cholinesterase activity in serum.

BACKGROUND OF THE INVENTION

In general, the concentration of cholinesterase (hereinafter referred to as ChE) in serum is known to be decreased, for example, in a patient with liver disease, while it is known to be increased, for example, in a patient with kidney disease. Therefore, these disease can be diagnosed by determining the cholinesterase activity in serum of these patients and determination method which permits exact determination of cholinesterase activity in serum can be used for clinical examinations.

As method for determining cholinesterase activity in serum, there have heretofore been reported various methods using a synthetic substrate, and some of them have been made practicable for daily clinical examinations. Examples of the heretofore well-known determination methods include (a) gas analysis method, (b) pH meter method, (c) pH-indicator colorimetric method, (d) thiocholine color formation methods, (e) enzymatic method, (f) UV method, etc.

(a) The gas analysis method [R. Ammon: Pflügers Arch. Ges Physiol., 233, 487 (1933)]comprises using acetylcholine as a synthetic substrate, bringing acetic acid produced by the enzymatic action of ChE into contact with sodium hydrogen carbonate, and quantitatively determining carbon dioxide gas produced.

(b) The pH meter method [H. O. Michel: J. Lab. & Clin. Med., 34, 1564 (1949)], like the gas analysis method, comprises using acetylcholine as a synthetic substrate, and measuring a pH change due to acetic acid produced by the enzymatic action of ChE by means of pH meter.

(c) The pH-indicator colorimetric method, unlike the pH meter method, comprises using acetylcholine as a synthetic substrate, and measuring a pH change due to acetic acid produced by ChE in terms of the molecular absorbance of the indicator. As the indicator, there are used phenol red [Hiroshi Takahashi and Susumu Shibata, IGAKU-TO-SEIBUTSUGAKU (Medicine and Biology), 20, 96 (1959)], bromothymol blue [H. G. Biggs, et al., Amer. J. Clin. Path., 30, 181 (1958)], m-nitrophenol [Tadahide Sasaki, RINSHO-BYORI (chemical Pathology), 12, 555 (1964)], etc.

(d) The thiocholine method [P. Garry, J. Clin. Chem., 11, (2), 91 (1965)]uses acetylthiocholine, butylthiocholine or the like as a substrate. These substrate yields thiocholine by the enzymatic reaction of ChE, and then this thiocholine reacts with 5,5'-dithiobis-2-nitrobenzoic acid (DTNB) to produce a yellow color. The thiocholine method comprises measuring this yellow color by means of a colorimeter.

(e) The enzymatic method comprises using benzoylcholine [Hirosaki Okabe et al, RINSHO-BYORI (clinical Pathology), 25, 751 (1977)], orthotoluoylcholine [Japanese Patent Application Kokai (Laid-Open) No. 138533/79]or the like as a substrate, converting chlorine produced by the enzymatic action of ChE into betaine by cholineoxidase, and subjecting 4-aminoantipyrine to oxidative condensation reaction with phenol or the like by thus produced hydrogen peroxide in the presence peroxidase to cause color production.

(f) The UV method includes two kinds of methods, and the one is a method of W. Kalow using benzoylcholine as a substrate [W. Kalow and K. Genet, Can. J. Biochem. & Physiol., 35, 339 (1975)], the another is a method using p-hydroxy-benzoylcholine [Japanese Patent Application Kokai (Laid-Open) Nos. 110198/82 and 129999/83]as a substrate. The former comprises monitoring a decrease in amount of the substrate caused by its hydrolysis due to the enzymatic action of ChE at a determination wave length of 240 nm. The latter comprises reacting p-hydroxy-benzoate hydroxylase with p-hydroxybenzoic acid produced by the enzymatic action of ChE, in the presence of the coenzyme NADPH, and monitoring, at a wave length of 340 nm, a decrease of absorbance upon the oxidation of NADPH into NADP by this reaction.

However, these determination methods involve various defects and problems, which are responsible for the inaccuracy of the resulting determined value. These method, for example, the gas analysis method (a) and the pH meter method (b), are disadvantageous in that their operations are troublesome and involves practical problems of inability to deal with many samples, and the like. The pH-indicator colorimetric method (c) comprises simple operations and can deal with many samples, but it should be pointed out that this method is disadvantageous, for example, in that the reaction time is long and in that during the reaction, the pH is not kept constant and the obtained values is not sufficiently reproducible at low and high values.

Any of the above-mentioned methods (a) to (c) use acetylcholine as a substrate, and in the case of such methods, the substrate itself also is disadvantageous because acetylcholine tends to undergo nonenzymatic hydrolysis and has no high substrate specificity.

The thiocholine method (d) is advantageous, for example, in that it is excellent in reactivity, has a high sensitivity, comprises simple operations, can deal with many samples, and make it possible to carry out the determination also by an initial velocity method. However, it is seriously affected by bilirubin in serum because of the yellow coloration and unavoidably affected by compounds having a thiol group such as glutathione. Furthermore, it is disadvantageous, for example, in that the substrate itself is instable. These disadvantages are responsible for errors of obtained values.

In the enzymatic method (e), since the coloration is red, there is not interference by bilirubin in serum, and many samples can be dealt with. However, since phenol or 4-aminoantipyrine used as a reagent for the colorproducing system competitively inhibits ChE, the amount of these reagents used is greatly limited, so that sufficient color production is difficult. Also these enzymatic method utilizes hydrogen peroxide. In general, a determination method via hydrogen peroxide is unavoidably affected not only by bilirubine in serum, reducing substances such as ascorbic acid and the like but also by choline produced by decomposition of phospholipids or the like. In particular, the employment of benzoylcholine as a substrate involves various problems, for example, its non-enzymatic hydrolysis which causes troubles.

In the UV method (f), a method of W. Kalow, using benzoylcholine as substrate, measures directly a decrease in amount of the substrate. Consequently, the principle of determination of this method is simple and plain. However, this method is disadvantageous, for example, in that since the determination wave length is 240 nm, interference by serum components tends to occur, and in that since nonenzymatic hydrolysis of benzoylcholine tends to occur, the reaction can not be carried out in the optimum pH range of ChE. It is disadvantageous also, for example, in that since as the determination wave length there is used wave length at the slope of absorption spectrum of the substrate, resulting in a large deviation of absorption coefficient due to the deviation of wave length.

The UV method, using p-hydroxybenzoylcholine as a substrate, is an excellent method for determining ChE activity which makes it possible to carry out the reaction at a range of optimum pH, permits removal of the defects of the hydrogen peroxide coloration system, namely, removal of influence of bilirubin, reducing substance such as ascorbic acid and the like as well as interference by choline produced by decomposition of phospholipids, is free from the defects of the thiocholine method, and is applicable to an autoanalyzer capable of dealing with many samples. However, since NADPH, the coenzyme used, is an expensive reagent and is poor in stability, it is difficult to keep the coenzyme under a definite quality. Further, in this method, p-hydroxybenzoate hydroxylase, proto-catechuate 3,4-dioxygenase or the like is used as a reagent enzyme in the determination, therefore there are many factors which produce an error of the obtained value.

As described above, the conventional methods for determining the ChE activity involve various problems, and cause an error of the obtained value.

SUMMARY OF THE INVENTION

We have devoted ourselves to research in order to remove the defects of the conventional methods for determining ChE activity and have accomplished this invention. In other words, the present inventors have synthesized 6-acetoxymethyl-2-naphthoylcholine iodide (hereinafter referred to a AMNCI) which are a novel chemical compound, and as a result of investigation on the determination of ChE activity by a UV method using it as a substrate, we have found the following facts. A wave length of about 335 to about 355 nm can be used as the determination wave length, and are very stable to nonenzymatic hydrolysis and react specifically with ChE in serum, in particular, pseudocholinesterase, and therefore the employment of AMNCI permit very accurate and highly reproducible determination of ChE activity in serum which has also other various advantages. Based on the above findings, this invention has been accomplished.

That is to say, this invention is directed to a novel choline derivative represented by the general formula (I), and to a method for determining cholinesterase activity, characterized by using said novel choline derivative of the general formula (I) as a substrate,

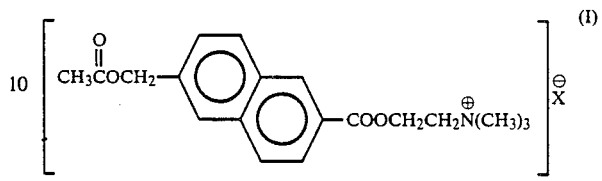

wherein X is a halogent atom.

X in the general formula (I) is a halogen atom such as iodine, chlorine, bromine, fluorine, and the like.

BRIEF DESCRIPTION OF DRAWING

FIG. 1 shows UV spectra of AMNCI (a) (concentration: 100 μM) and 6-acetoxymethyl-2-naphthoic acid (b) (concentration: 100 PM) measured in a 250 mM Tris-maleic acid buffer (pH 8.0, 25° C.). FIG. 7 is a graph showing the relationship between serum dilution and ChE activity. FIG. 8 shows a S-V curve and a Lineweaver-Burk plot.

DETAILED DESCRIPTION OF PREFERRED EMBODIMENTS

Figure 2:
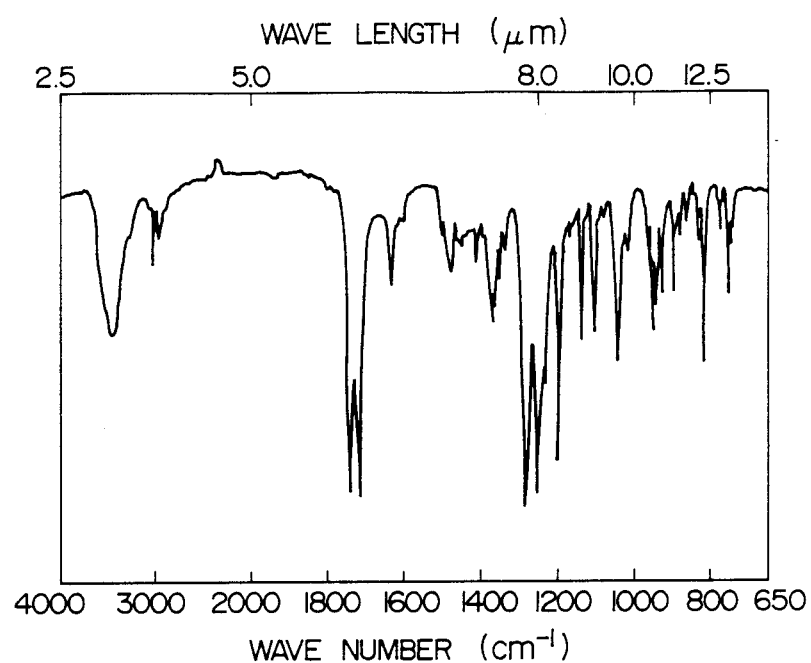
FIG. 2 shows an IR spectrum of AMNCI.

The novel choline derivative of the present invention can be prepared by reducing 2,6-dimethylnaphthoyl-carboxylate to obtain 6-hydroxymethylnaphthoic acid, acetylating the hydroxy moiety on 6-hydroxymethyl group of thus obtained compound, reacting the acetylated compound with 2-demethylaminoethanol, and then reacting the resulting compound with methyl halide such as methyl iodide, and the like.

The determination method of ChE activity utilizing novel choline derivative (AMNCI) of this invention is explained below.

UV spectra of AMNCI (a) and 6-acetoxymethyl-2-naphthoic acid (b) are shown in FIG. 1. Upon hydrolysis by the action of ChE, AMNCI gives choline and 6-acetoxy-methyl-2-naphthoic acid. Choline has no UV absorption at a wave length longer than 300 nm. 6-acetoxymethyl-2-naphthoic acid have almost no UV absorption at a wave length longer than 335 nm. On the other hand, AMNCI has UV absorption at a wave length shorter than 355 nm. Therefore, when AMNCI is used as a substrate for determining ChE activity and the reaction is monitored at a wave length of 335 to 355 nm, no serious interference by serum component occurs. Therefore, a decrease in amount of the substrate AMNCI can accurately determined, so that ChE activity can be accurately determined. AMNCI has also many advantages as described hereinafter.

Therefore, as a method for determining ChE activity using the novel choline derivative of the general formula (I), there is provided with this invention the method for determining ChE activity which comprises mixing a sample containing ChE with a novel choline derivative represented by the general formula (I), and then measuring optical absorbance, especially of that at a wave length of about 335 to about 355 nm.

In the UV method of W. Kalow mentioned hereinbefore, the determination wave length is 240 nm and hence serious interference by blood components occurs in initial absorptions. On the other hand, no serious interference occurs at the determination wave length of about 335 to about 355 nm for the substrate of this invention, so that ChE activity can be determined under the optimum determination conditions. In the UV method of W. Kalow, benzoylcholine used as a substrate has an absorption maximum near 230 nm in 1/15M phosphate buffer (pH 7.40), and the absorption curve has slope at the determination wave length of 240 nm. Therefore, the deviation of absorption coefficient due to the deviation of wave length is large. The novel substrate AMNCI has an absorption maximum near 335 nm, which fact makes it possible to set the determination wave length at an absorption peak. This suggests that the difference in absorption coefficient caused by the problem of low accuracy of determination wave length of analyzer becomes very small and the difference in the measured value among machines also becomes small.

Furthermore, since benzoylcholine receives substrate inhibition at the concentration of 50 $\mu$M or more, the enzyme reaction can not be carried out at high substrate concentration, resulting in a narrow range of linearity in absorption curve with the lapse of time, so that the determination can not be carried out up to a high unit of ChE activity. In contrast, the novel substrate of this invention do not receive substrate inhibition until the substrate concentration of 300 $\mu$M, and therefore the reaction can be carried out at high substrate concentration in the reaction system (see FIG. 8).

Further, the novel substrate AMNCI is very stable to nonenzymatic hydrolysis. For example, hydrolysis hardly occurred in a 250 mM Tris-maleic acid buffer, pH 8.0, at 37° C. for 60 minutes (see FIG. 6). This result indicates that nonenzymatic hydrolysis is negligible in the determination, and that ChE activity can be determined accurately.

As a buffer for keeping the pH of a reaction system constant, there may be used barbiturates, phosphates, pyrophosphates, glycine, glycylglycine, tris (hydroxymethyl) aminomethane, etc. Any buffer other than those buffer may be used so long as it can retain its capacity as buffer in the pH range from 7.5 to 10.0.

The Michaelis constants (Km value) of AMNCI for ChE is substantially the same as that of benzoylcholine and is about $5 \times 10^{-5}$ ($1/20 \times 10^{-3}$) mol/l in a 250 mM Tris-maleic acid buffer (pH 8.0) (see FIG. 8). The Km value of AMNCI is small enough for the reaction to be carried out at high substrate concentration in the reaction system of the determination method of this invention, and the range of linearity in absorption curve with the lapse of time is enlarged, so that the determination can be sufficiently carried out for a high unit of ChE activity.

Figure 4:
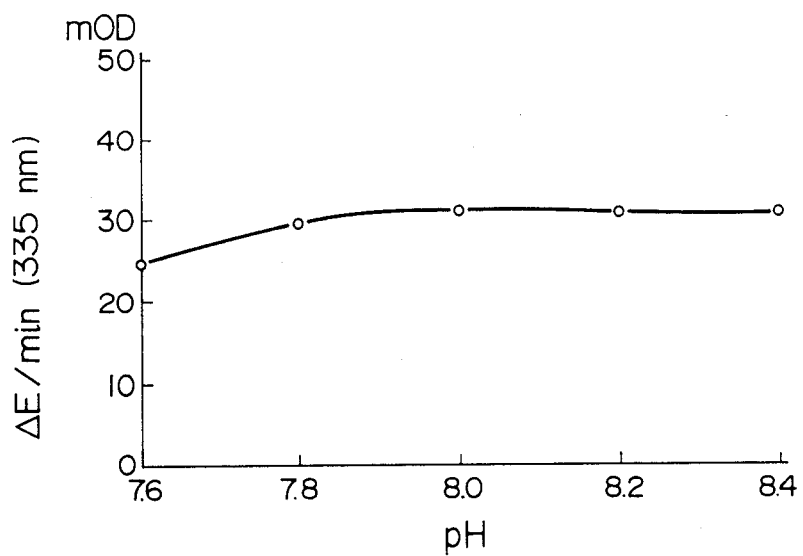
FIG. 4 is a graph showing the optimum pH of ChE.

When AMNCI is used as a substrate, the optimum pH of ChE is near 8.0 in a 250 nM tris-maleic acid buffer (see FIG. 4). As described hereinbefore, AMNCI is stable to nonenzymatic hydrolysis at pH 8.0, and hence the determination method of this invention makes it possible to carry out the enzyme reaction at the optimum pH of ChE.

As cholinesterases, there are known two kinds, namely, pseudo-ChE existing in serum and true-ChE existing in erythrocyte. The cholinesterase whose activity is usually determined in a clinical examination is pseudo-ChE in serum, but since serum is contaminated with true-ChE in some cases, a substrate which reacts selectively with pseudo-ChE alone is preferably. AMNCI used in the method of this invention is a substrate having a very high specificity which reacts well with pseudo-ChE but hardly reacts with true-ChE.

Embodiments of the method for determining ChE activity of this invention are shown in detail in the Examples described hereinafter, and the procedures used in a conventional UV method may be also employed in this invention.

The method for determining ChE activity of this invention is free from the various problems of the conventional methods. The advantages of this invention are as described below.

(1) The reaction mechanism of the determination system is simple and plain, and there are very few causes of error in the obtained value.

(2) The determination can be carried out at the wave length of a peak of absorption curve (335 nm).

(3) Since AMNCI used as a substrate in the invention is stable to nonenzymatic hydrolysis, the reproducibility of the obtained value is very high.

(4) AMNCI has a high substrate specificity for pseudo-ChE.

(5) Since it is unnecessary to employ a sample blank for each sample, the determination can be carried out easily and rapidly, so that many samples can be dealt with at once.

(6) Since AMNCI is stable, the enzyme reaction can be carried out at the optimum pH (8.0 - 8.2) for ChE.

(7) Since AMNCI does not receive substrate inhibition, the reaction can be carried out at high substrate concentration.

(8) The determination is possible up to a high unit of ChE activity.

As described above, the method for determining ChE activity of this invention is free from the defects of the conventional methods, has many advantages and characteristics, permits accurate and simple determination of ChE activity, and can significantly contribute to the determination of ChE activity in daily clinical examinations. Accordingly, the method for determining ChE activity of this invention is very useful as a method for determining the ChE activity in serum of normal persons, patients with liver disease, patients with kidney disease, etc.

This invention is further explained below in more detail with reference to Examples, which are not by way of limitation but by way of illustration.

EXAMPLE 1

Synthesis of 6-Acetoxymethyl-2-naphthoilcholine Iodide (AMNCI)

A solution of 21.6 g of 2,6-naphthalene dicarboxylic acid and 28.5 g of thionyl chloride in 200 ml of dried benzene containing 1 drop of pyridine was refluxed for 2 hours, after which the solvent was concentrated to obtain 23 g of 2,6-naphthoil dichloride. This substance was refluxed in 500 ml of dried methanol for 2 hours, the resulting precipitates were collected by filtration to obtain 19 g of 2,6-dimethylnaphthalene dicarboxylate. In 500 ml of 50% ethanol was suspended this product, followed by adding thereto 30 g of NaBH₄, and reduction was carried out to obtain 12 g of 6-hydroxymethyl-2-naphtoic acid. To this substance was added 11.9 ml of acetic anhydride and 1 drop of conc. sulfuric acid. The resulting mixture was refluxed for 30 minutes to obtain 10 g of 6-acetoxymethyl-2-naphthoic acid, m.p. 180°-190° C.

| Elementary analysis for C₁₄H₁₂O₄ (M.W. 244.250) | | |
| --- | --- | --- |
| Found (%) | C: 69.03 | H: 4.83 |
| Calculated (%) | C: 68.85 | H: 4.95 |

A solution of 8.4 g of 6-acetoxymethyl-2-naphthoic acid in 150 ml of dried toluene containing 5.4 ml of thionyl chloride and 1 drop of pyridine was refluxed for 30 minutes, cooled, and then the resulting mixture was filtered. The solvent of filtrate was distilled off under reduced pressure to obtain 8.5 g of 6-acetoxymethyl-2-naphthoilchloride. This substance was dissolved in 50 ml of dried toluene, and the resulting solution was added dropwise to a solution of 7 ml of 2-dimethylaminoethanol in 150 ml of dried toluene, with cooling to 5° to 10° C. Thereafter, the resulting mixture was stirred overnight at room temperature and subsequently washed with water and then with a saturated aqueous sodium chloride solution. The toluene phase was dried over anhydrous magnesium sulfate, and then the solvent was distilled off under reduced pressure to obtain 8.5 g of an oily substance. This substance was dissolved in 200 ml of acetone, followed by adding thereto a solution of 3.7 g of methyl iodide in 50 ml of ethyl acetate, and the solution is permitted to stand with cooling, after which the catalyst precipitated was collected by filtration, washed with acetone, and then dried in vacuo over phosphorus pentaoxide to obtain 10.2 g of 6-acetoxymethyl-2-naphthoilcholine iodide (AMNCI), m/p. 182°-184° C. These crystals gave a single spot (Rf =0.36) in a silica gel thin layer chromatography (n-butanol:acetic acid:water =4:1:2).

| Elementary analysis for C₁₉H₂₄NO₄I (M.W. 457.312) | | | |
| --- | --- | --- | --- |
| Found (%) | C: 49.72 | H: 5.36 | N: 3.06 |
| Calculated (%) | C: 49.90 | H: 5.29 | N: 3.06 |

UV spectra and IR spectra of the product synthesized are shown in FIG. 1 and 2, respectively.

EXAMPLE 2

Figure 3:
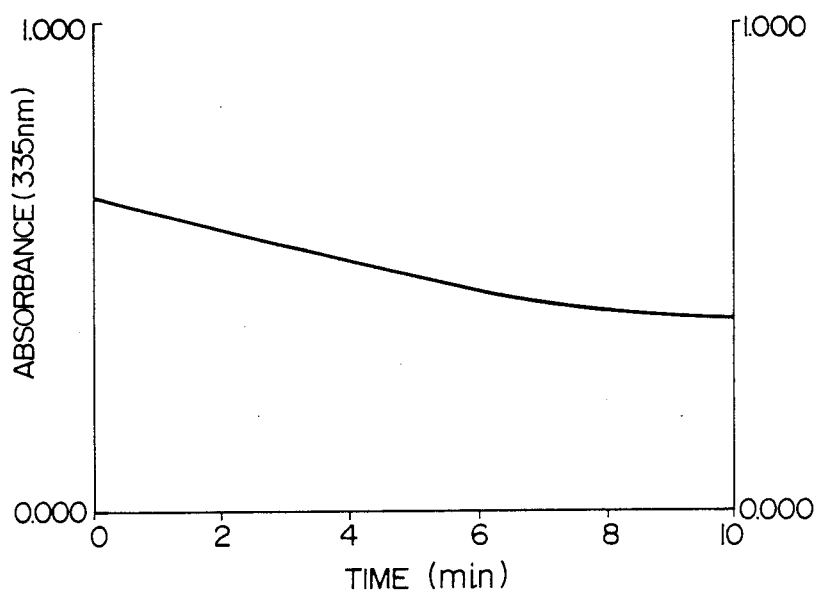
FIG. 3 shows time course of ChE activity in serum by the use of AMNCI as a substrate.

Method for Determining ChE Activity in Serum:

(1) a 250 mM Tris-maleic acid buffer, pH 8.0 (25° C.)
(2) a sample
(3) a 1.3 mM aqueous substrate (AMNCI) solution To the 2.0 ml of the buffer (1) was added 0.10 ml of the sample, and preheating was conducted at 37° C. for about 2 to 10 minutes. Thereto was added 0.5 ml of the substrate solution (3), a stop watch was started at the same time and then subjected to determination of optical absorbance at a wave length of 335 nM after 20 second and 80 second exactly to obtain the change per minute of optical absorbance. FIG. 3 shows time course.

As the sample (serum), CONSERA I (manufactured by Nissui Pharmaceutical Co., Ltd.) was used. The ChE activity value is calculated from the following equation.

$$IU/l = \frac{\Delta O.D./min^{(1)} \times \left[\begin{array}{c}\text{Amount of} \\ \text{reaction solution}\end{array}\right] \times 10^6}{\left[\begin{array}{c}\text{Molecular absorption}^{(2)} \\ \text{coefficient}\end{array}\right] \times \left[\begin{array}{c}\text{Amount of} \\ \text{serum}\end{array}\right]}$$

(1) ΔO.D. is a change per minute of optical absorbance at a wave length of 335 nm.
(2) The molecular absorption coefficient at 335 nm is 1195.

From the above equation, the serum used was (IU/l) unit. As shown in FIG. 3, linearity without time lag with the lapse of time was observed up to 7 minutes at 690 (IU/l) of ChE unit. This fact indicates that autoanalyser may be usable.

EXAMPLE 3

The pH of the buffer (1) in Example 2 was varied from 7.6 to 8.4 and the optimum pH for ChE in said method was determined. This determination was carried out entirely according to Example 2 except for the pH of the buffer. The result obtained is shown in FIG. 4. Under these conditions, the optimum pH was 8.0.

EXAMPLE 4

Figure 5:
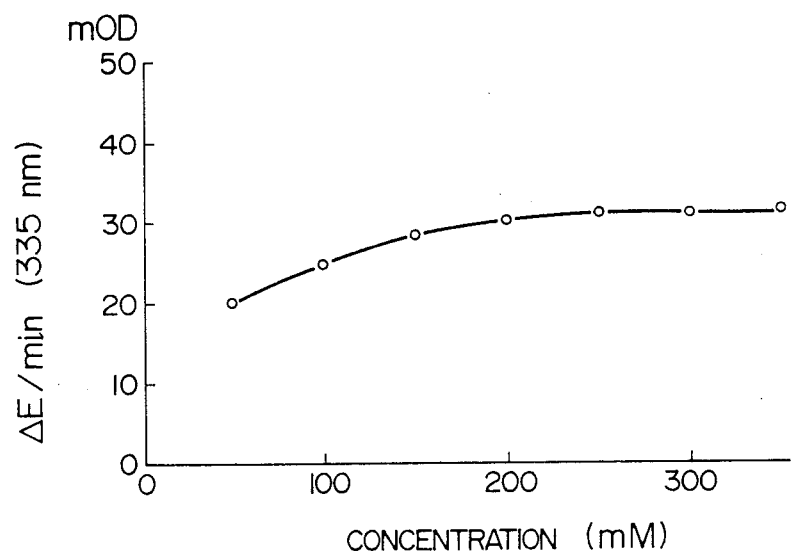
FIG. 5 is a graph showing the effect of buffer concentration on ChE activity.

The concentration of the buffer (1) in Example 2 was varied from 50 mM to 300 mM and the optimum concentration for buffer in said method was determined. This determination was carried out entirely according to Example 2 except for the concentration of the buffer. The result obtained is shown in FIG. 5. Under these conditions, the optimum concentration of the buffer was 200 mM to 300 mM.

EXAMPLE 5

Figure 6:
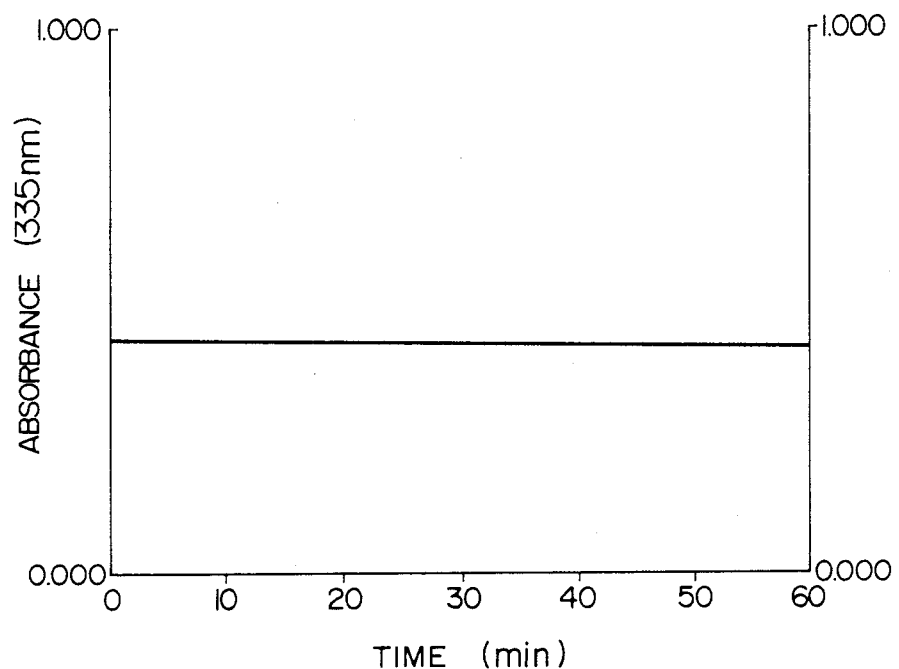
FIG. 6 is a graph showing the stability of AMNCI to nonenzymatic hydrolysis.

To 2.0 ml of the buffer (2) in Example 2 was added 0.5 ml of the substrate solution (3), and the resulting solution was placed in a heat insulating cuvette having a temperature of 37° C. The change of optical absorbance at a wave length of 335 nm was monitored with the lapse of time, whereby the stability of the substrate to nonenzymatic hydrolysis was examined. As a result, the substrate was almost stable up to 60 minutes as shown in FIG. 6. Since the substrate AMNCI is stable at the optimum pH of 8.0, it is unnecessary to measure a reagent blank value for each sample.

EXAMPLE 6

The substrate specificity was examined according to the determination method in Example 2. As the sample, pseudo-ChE (manufactured by Sigma) 10 U/ml and true-ChE (manufactured by Sigma) 10 U/ml were used. Reducing rate of optical absorbance (ΔE/min) was 0.0470 for pseudo-ChE, and 0.0005 for true-ChE, respectively. The reactivity ratio of pseudo-ChE to true ChE, obtained from reducing rate of optical absorbance, was about 1:0.01. This fact indicates that the substrate specificity of AMNCI is very high.

EXAMPLE 7

The relationship between dilution of serum and the ChE activity was examined according to Example 2. The serum was diluted with a physiological saline containing 5% albumine. As shown in FIG. 7, the serum dilution and the ChE activity are proportional in the manner of a straight chain passing through the origin.

This fact reveals that the ChE activity can be widely determine from low unit to high unit.

EXAMPLE 8

The substrate solution (3) in Example 2 was used as suitable dilute solutions, lineweaver-Burk plot were obtained from these solutions. Km value for the substrate of this invention, $5 \times 10^{-5}$ mol/l was calculated from the above-mentioned plot (see FIG. 8). From this fact, it is revealed that the substrate of this invention has high affinity for ChE, and has sufficient adaptability for this reaction system.

What is claimed is:

1. A novel choline derivative represented by the general formula (I),

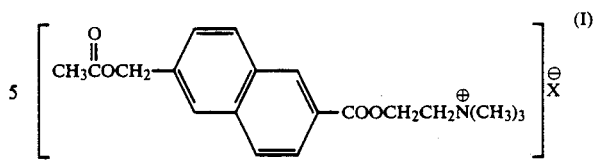

wherein X is a halogen atom.

2. A method for determining cholinesterase activity which comprises admixing a sample containing cholinesterase with a substrate, a novel choline derivative represented by the general formula (I),

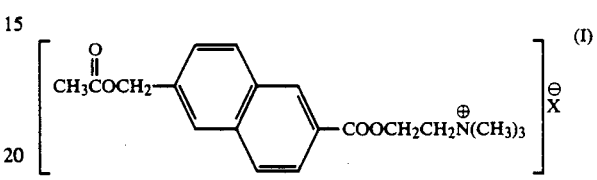

wherein X is a halogen atom, and measuring the optical absorbance of the reaction product therefrom.

3. The method according to claim 2, wherein the substrate is 6-acetoxymethyl-2-naphthalylcholine iodide.

4. The method according to claim 2, wherein the optical absorbance at a wave length of about 335 to about 355 nm is measured.

* * * * *